United States Patent
Tsukagoshi et al.

(10) Patent No.: US 6,990,168 B2
(45) Date of Patent: Jan. 24, 2006

(54) X-RAY CT SCANNER AND IMAGE PROCESSOR

(75) Inventors: Shinsuke Tsukagoshi, Otawara (JP); Tatsuro Suzuki, Utsunomiya (JP); Akira Adachi, Otawara (JP); Satoshi Saito, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 195 days.

(21) Appl. No.: 10/725,452

(22) Filed: Dec. 3, 2003

(65) Prior Publication Data
US 2004/0120451 A1    Jun. 24, 2004

(30) Foreign Application Priority Data
Dec. 4, 2002    (JP)    ................ 2002-352446

(51) Int. Cl.
 G21K 1/12    (2006.01)
(52) U.S. Cl. ................ 378/4; 378/901; 382/298; 345/660
(58) Field of Classification Search ................ 378/4, 378/15, 19, 62, 98.8, 901; 382/298, 299, 382/300; 345/660, 667, 668, 669, 670, 671
See application file for complete search history.

(56) References Cited

U.S. PATENT DOCUMENTS
2004/0169668 A1 *    9/2004    Yamada et al. ............ 345/660

FOREIGN PATENT DOCUMENTS
JP    2003-19131    1/2003

* cited by examiner

Primary Examiner—Edward J. Glick
Assistant Examiner—Courtney Thomas
(74) Attorney, Agent, or Firm—Oblon, Spivak, McClelland, Maier & Neustadt, P.C.

(57) ABSTRACT

An X-ray CT (computed tomography) scanner includes a gantry for collecting projection data about a patient, a reconstruction portion for reconstructing multislice image data or volumetric image data from the projection data at a given matrix size, a storage portion for storing the reconstructed image data, an input portion for entering a user's instruction regarding magnification or demagnification of image, and an image processing portion for converting the matrix size of the stored image data into a matrix size corresponding to the user's instruction and varying the image slice thickness of the stored image data into an image slice thickness corresponding to the user's instruction.

20 Claims, 4 Drawing Sheets

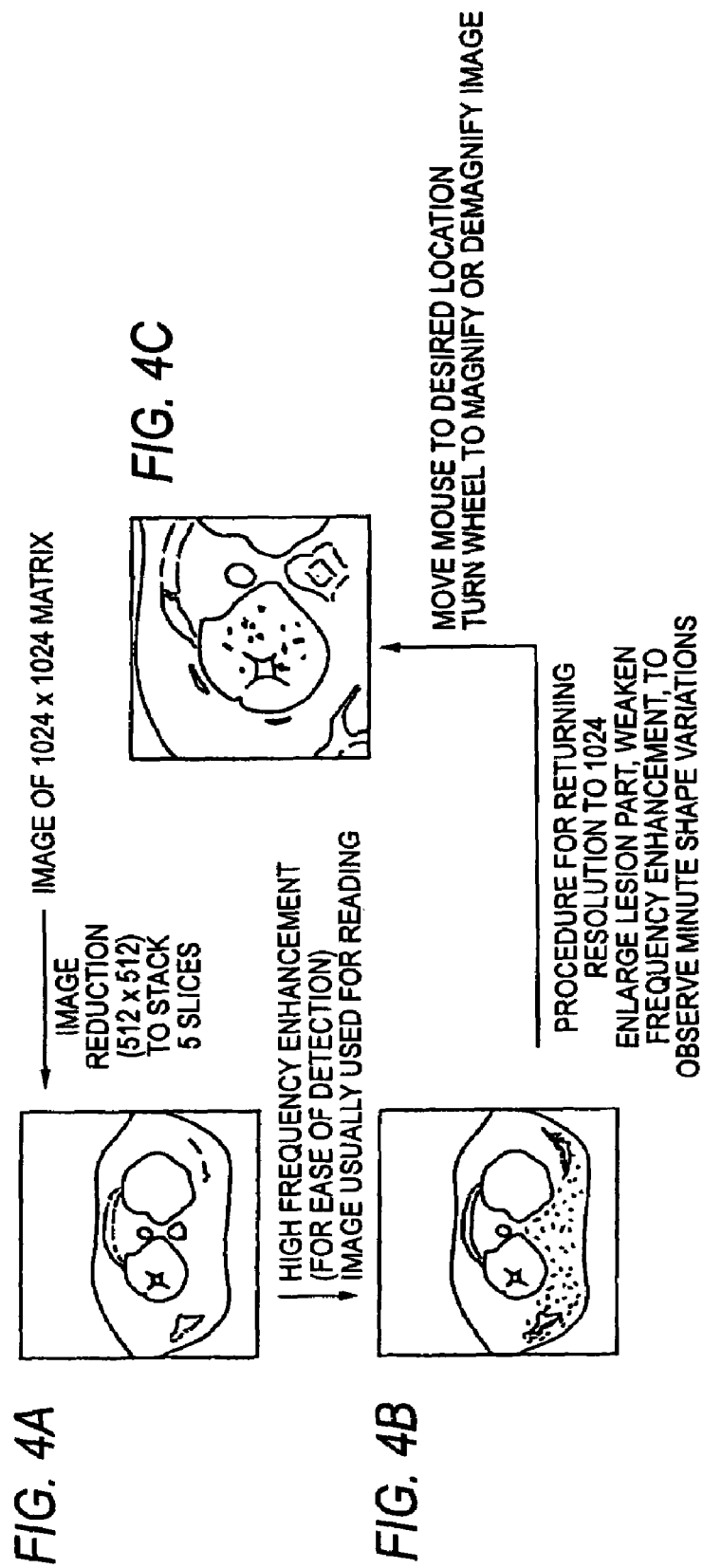

X-RAY CT SCANNER AND IMAGE PROCESSOR

CROSS-REFERENCE TO RELATED APPLICATIONS

This application is based upon and claims the benefit of priority from the prior Japanese Patent Application No. 2002-352446, filed Dec. 4, 2002, the entire contents of which are incorporated herein by reference.

BACKGROUND OF THE INVENTION

1. Field of the Invention

The present invention relates to an X-ray computed tomography (CT) scanner and image processor for reconstructing image data based on projection data taken from a patient to be examined from multiple directions.

2. Description of the Related Art

In recent years, display monitors have tended to have higher resolutions, decreased size, and reduced thickness. Also, their prices have declined. These trends have promoted adoption of filmless technology in the field of medical imaging diagnostics. The merits of filmless capabilities are not limited to direct consequences such as cost of film itself and the cost spent for storage space. In the field of medical imaging diagnostics, filmless technology offers the advantages that the diagnostic accuracy is improved.

For example, an X-ray computed tomography (CT) scanner stores projection data collected by multislice scans or helical scans. When diagnostic reading is done, the CT scanner reconstructs tomographic image data from the projection data according to reconstruction conditions specified by a human operator such as slice position, resolution, and image slice thickness and displays images. During diagnostic reading, the operator can observe any desired tomographic image while varying the slice position, resolution, and image slice thickness at will. In this respect, it is expected that the X-ray CT scanner provides much improved diagnostic accuracy compared with film-based reading in which the slice position, resolution, and image slice thickness are fixed since printed images are used.

However, this filmless technology has problems to be solved. An actual diagnostic reading session generally starts with reconstructing an image that covers a wide area with a very large image slice thickness and at a low resolution of about 512×512 pixels, for example. The image is then displayed. A judgment is made on this wide-area image as to whether there is any lesion. If any portion that is a suspicious lesion is discovered, the image slice thickness is reduced. Alternatively, the resolution is enhanced, and the display FOV is reduced, for example. An accurate image of 512×512 pixels is reconstructed. This portion of image and surrounding portions are displayed over the whole monitor screen while maintaining the high resolution. Consequently, the legion can be identified more accurately. Furthermore, depending on the doctor, it is necessary to check the tissue structure of the lesion in detail. In this case, a more accurate image may be reconstructed by reducing the image slice thickness further and setting the resolution to a smaller display FOV, for example, and the image may be displayed.

In this way, lesional areas are narrowed down while increasing the resolution and reducing the image slice thickness gradually. Whenever the resolution and image slice thickness are varied, the reconstruction processing is repeated. The reconstruction processing is one of the most time-consuming processes. Therefore, the efficiency of the diagnostic reading work deteriorates. Especially, this technology is unsuited for screening examinations for many patients.

BRIEF SUMMARY OF THE INVENTION

It is an object of the present invention to provide an X-ray computed tomograph (X-ray CT scanner) and image processor providing improved efficiency of diagnostic reading work.

An X-ray CT scanner according to a first aspect of the invention has a gantry for collecting projection data about a patient, a reconstruction portion for reconstructing multislice image data or volumetric image data from the projection data at a given matrix size, a storage portion for storing the reconstructed image data, an input portion for entering a user's instruction regarding magnification or demagnification of image, and an image processing portion for converting the matrix size of the stored image data into a matrix size corresponding to the user's instruction and varying the image slice thickness of the stored image data into an image slice thickness corresponding to the user's instruction.

An image processor according to a second aspect of the invention has a storage portion for storing multislice image data or volumetric image data about a patient, an input portion for entering a user's instruction regarding magnification or demagnification of image, and an image processing portion for converting the matrix size of the stored image data into a matrix size corresponding to the user's instruction and varying an image slice thickness of the stored image data into an image slice thickness corresponding to the user's instruction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 4A to 4C schematically illustrate the flow of processing for diagnostic reading illustrated in FIG. 3, together with examples of image.

DETAILED DESCRIPTION OF THE INVENTION

Figure 1:
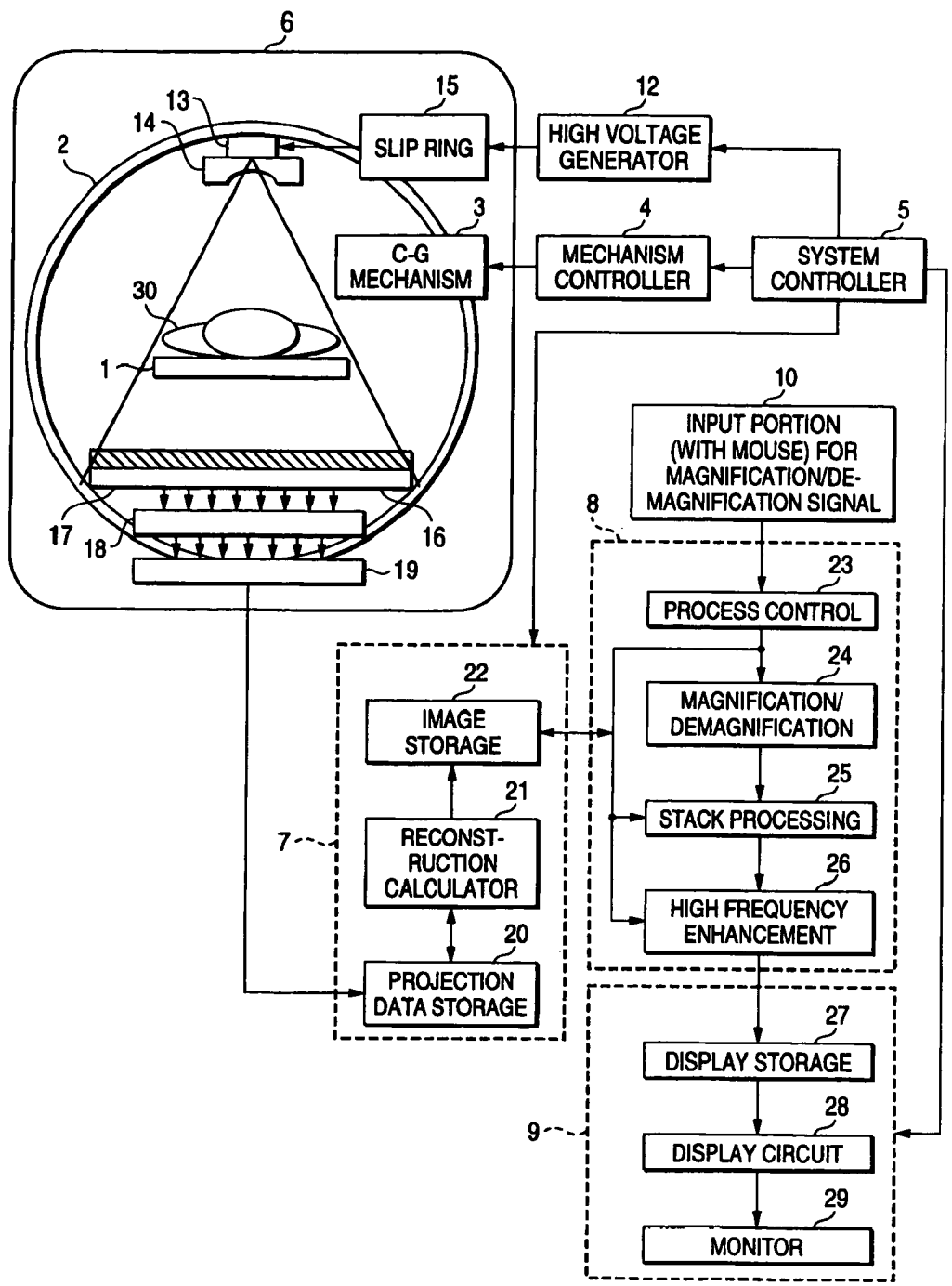
FIG. 1 is a structural view of a CT scanner according to an embodiment of the present invention.

Embodiments of an X-ray CT scanner and image processor according to the present invention are hereinafter described with reference to the drawings. X-ray CT scanners have various types including a rotation/rotation type in which an X-ray tube and a radiation detector rotate together around a patient and a stationary/rotation type in which a number of detection elements are arrayed annularly and only an X-ray tube rotates around a patient. The invention can be applied to either type. In the following description, the X-ray CT scanner is assumed to be of the rotation/rotation type that prevails today. Furthermore, to reconstruct tomographic image data about 1 slice, projection data derived by one full rotation around the patient, i.e., about 360°, is necessary. Furthermore, in the half scan method, projection data derived by a rotation of 180°+ view angle is needed. The invention can be applied to either reconstruction method. In the following description, an example in which tomographic image data is reconstructed from about 360° of projection data as in the former case is taken. One prevalent mechanism of converting incident X-rays into charge is the indirect conversion type in which the X-rays are converted into light by a fluorescent material such as a scintillator and the light is then converted into electric charge by a photoelectric device such as a photodiode. The other is the direct conversion type utilizing creation of electron-hole pairs within a semiconductor in response to X-rays and movement of the pairs to the electrodes, i.e., photoconductive phenomenon. The X-ray detecting device may adopt either type. In this description, the former indirect conversion type is used. In recent years, X-ray CT scanners of a so-called multiple-tube type in which pairs of X-ray tubes and X-ray detectors are installed on a rotating ring have been commercialized to a significant extent. Its peripheral techniques have been also developed to a considerable extent. The present invention can be applied to both the prior single-tube X-ray CT scanner and multiple-tube X-ray CT scanner. In this description, the scanner is of the single-tube type.

A tomographic image is a representation of a cross section of a tissue having some thickness. The thickness of the cross section of the tissue is referred to as the slice thickness. X-rays spread radially from the focus of the X-ray tube, pass through the patient, and arrive at the X-ray detectors. Accordingly, the thickness of the X-rays increases with moving away from the focus of the X-ray tube. Customarily, the thickness of the X-ray at the center axis of rotation is defined to be the slice thickness. In this description, the thickness of X-rays at the center axis of rotation is referred to as the slice thickness according to the customary usage. This convention is also applied to the width of the detection device as viewed in the direction of slice. That is, where a detection device is expressed as having a sensitive width corresponding to some slice thickness, the sensitive width is greater than the slice thickness in practice. More specifically, it is necessary in practice to design the sensitive width to be greater than the slice thickness according to the ratio of the distance between the focus of X-rays and the detection device to the distance between the focus of X-rays and the center axis of rotation.

FIG. 1 is a block diagram showing the configuration of a computed tomography apparatus (CT scanner) according to the present embodiment. This scanner has a gantry 6 fitted with an annular rotating frame 2. This frame 2 is rotatably supported to a couch-gantry mechanism portion 3, which has a motor for producing a power to rotate the rotating frame 2. The motor is supplied with electric power from a mechanism control portion 4 and produces a power. An X-ray tube 13 and an X-ray detector 16 are installed on the rotating frame 2, the detector 16 having an array of detector elements. The X-ray detector 16 is placed opposite to the X-ray tube 13 via a patient 30 placed on the couch 1. A high voltage generator 12 applies a high voltage between the cathode of the X-ray tube 13 and the rotating anode, and supplies heating current to the cathode filament of the tube 13. Thermal electrons emitted from the heated filament are accelerated by the high voltage and collide against the target of the rotating anode, thus producing X-rays. To permit continuous rotation, the X-ray tube 13 is connected with the high voltage generator 12 via a slip ring 15. The mechanism control portion 4 and high voltage generator 12 supply electric power to the motor of the couch-gantry mechanism portion 3 to perform scans under control of a system control portion 5 for data collection from multiple directions. The mechanism control portion 4 and high voltage generator 12 also apply a tube voltage and supply a filament-heating current to the X-ray tube 13.

A data acquisition system (DAS) 18 is connected with the X-ray detector 16 via switches 17. The acquisition system 18 has plural channels of integrators for integrating the output current or voltage signal delivered from the X-ray detector 16, preamplifiers for amplifying the output signals from the integrators, and analog-to-digital converters for converting the output signals from the preamplifiers into digital signals.

The data acquisition system 18 is connected with an image creating portion 7 via a noncontacting data transfer circuit 19 utilizing light or magnetism. The output data from the data acquisition system 18 is generally referred to as raw data. Usually, the raw data undergoes various kinds of preprocessing such as correction for achieving sensitivity uniformity between the channels. The preprocessed raw data is generally referred to as projection data. The image creating portion 7 has a projection data storage circuit 20, which preprocesses raw data transmitted from the data acquisition system 18 via the data transfer circuit 19 and stores the preprocessed data as projection data. A reconstruction calculation circuit 21 reconstructs tomographic image data based on the stored projection data. The tomographic image data is reconstructed as multislice data or volume data. Tomographic image data is reconstructed at the maximum resolution (maximum matrix size) determined by the number of channels in the X-ray detector 16, the channel pitch, the sampling frequency for data collection, the reconstruction function of the reconstruction calculation circuit 21, and other factors. The tomographic image data is reconstructed with the smallest image slice thickness or minimum voxel size determined by the helical pitch, data interpolation method, reconstruction method, and other factors. An image storage circuit 22 stores the tomographic image data reconstructed by the reconstruction calculation circuit 21.

An image processing portion 8 is connected with the image creating portion 7, and has an image processing control circuit 23, an image magnification-demagnification circuit 24, a stack processing circuit 25, and a high-frequency enhancement circuit 26. An input portion 10 for entering a user's instruction regarding magnification or demagnification of image is connected with the image processing control circuit 23. An image magnification factor is entered as the user's instruction. An applicable method is selected as the input method from various methods. For example, the numerical value of the image magnification factor is entered. The image magnification factor is entered by selectively clicking on plural buttons corresponding to plural image magnification factors displayed on the viewing screen. Where a mouse with a wheel is adopted in the input portion 10, an image magnification factor corresponding to the rotational angle of the wheel is entered.

Figure 2:
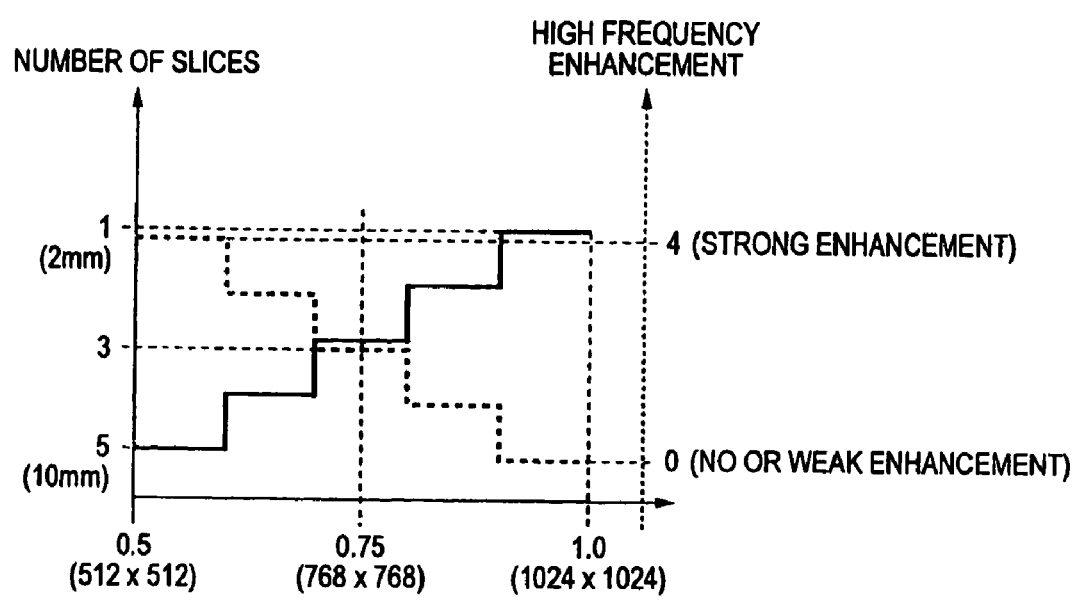
FIG. 2 is a graph in which the number of stacked slices and the degree of enhancement of high-frequency components are plotted against the image display magnification factor controlled by the image processing control circuit shown in FIG. 1.

The image magnification-demagnification circuit 24 converts the matrix size of the tomographic image data stored in the image storage circuit 22 into a matrix size corresponding to the image magnification factor entered via the input portion 10 under control of the image processing control circuit 23. An image magnification factor is selected from a range from 0.5 to 1.0 (magnification of unity) and entered as shown in FIG. 2, for example. As an example, it is assumed that tomographic image data is reconstructed with a matrix size of 1024×1024 pixels and stored in memory. When a magnification factor of 0.5 is entered, the tomographic image data is converted into a matrix size of 512×512 pixels. When a magnification factor of 1.0 is entered, the tomographic image data is maintained at the matrix size of 1024×1024 pixels. The matrix size is converted by general image enlargement processing such as a method of thinning out pixels or a method of taking the average of the sum of plural pixels.

In the following description, it is assumed that the matrix size of 1024×1024 pixels is the maximum matrix size (highest resolution) overall determined by the number of channels in the X-ray detector 16, the channel pitch, the sampling frequency for data collection, the reconstruction function of the reconstruction calculation circuit 21, and other factors.

The stack processing circuit 25 stacks sets of tomographic image data which have been converted in matrix size by the image magnification-demagnification circuit 24 for plural frames under control of the image processing control circuit 23. The number of the sets of tomographic image data corresponds to the number of stacked slices, which in turn corresponds to the image magnification factor entered via the input portion 10. As a result, the image slice thickness of the stored image data is converted into an image slice thickness corresponding to the entered image magnification factor.

Where the image data has been reconstructed as volume data and stored in memory, the stack processing circuit 25 converts the initial image slice thickness (voxel thickness) into an image slice thickness corresponding to the entered image magnification factor by multiplanar reconstruction (MPR) rather than by stack processing. In the following description, it is assumed that the image slice thickness is modified by stack processing.

The number of stacked slices is determined by the image processing control circuit 23 according to the image magnification factor that is a user's instruction entered via the input portion 10. For example, as shown in FIG. 2, the number of slices is increased in a stepwise fashion with reducing the entered image magnification factor, and vice versa. Where an image magnification factor of 0.5 is entered, the number of slices is set to 5. Sets of tomographic image data about 5 consecutive slices around the slice position are stacked together (images are stacked together). In this case, if the reconstruction calculation circuit 21 reconstructs the tomographic image data with an image slice thickness of 2 mm, for example, the tomographic image data stacked together with the number of slices "5" correspond substantially to an image slice thickness of 10 mm. When a magnification factor of "1.0" is entered, the number of slices is set to a minimum value of "1". No stacking is done. The image slice thickness of the tomographic image data is maintained at 2 mm that was used during reconstruction.

The high-frequency enhancement circuit 26 is substantially constructed as a non-recursive digital filter or recursive digital filter. The high-frequency enhancement circuit 26 enhances high-frequency components of the spatial frequencies about the tomographic image data created by the stack processing circuit 25 to an extent corresponding to the magnification factor entered via the input portion 10 under control of the image processing control circuit 23. The extent of enhancement performed by the high-frequency enhancement circuit 26 can be varied by switching coefficient sets applied to plural multipliers in the high-frequency enhancement circuit (digital filter) 26 from the image processing control circuit 23. The image processing control circuit 23 previously holds plural coefficient sets and supplies the coefficient sets selectively to the high-frequency enhancement circuit 26 according to the magnification factor entered via the input portion 10. In practice, the coefficient sets are correlated to the magnification factor such that the high-frequency components are enhanced to a greater extent with reducing the entered magnification factor and vice versa. For example, as shown in FIG. 2, when a magnification factor of "1.0" is entered, a coefficient set having such characteristics that the high-frequency components are hardly enhanced is selected. When a magnification factor of "0.5" is entered, a coefficient set showing the greatest extent of high-frequency enhancement among the plural coefficient sets is selected.

A display portion 9 is connected with the image processing portion 8. Tomographic image data created by the image processing portion 8 is displayed as a gray-scale image on a monitor 29 via a display storage circuit 27 and a display circuit 28.

Figure 3:
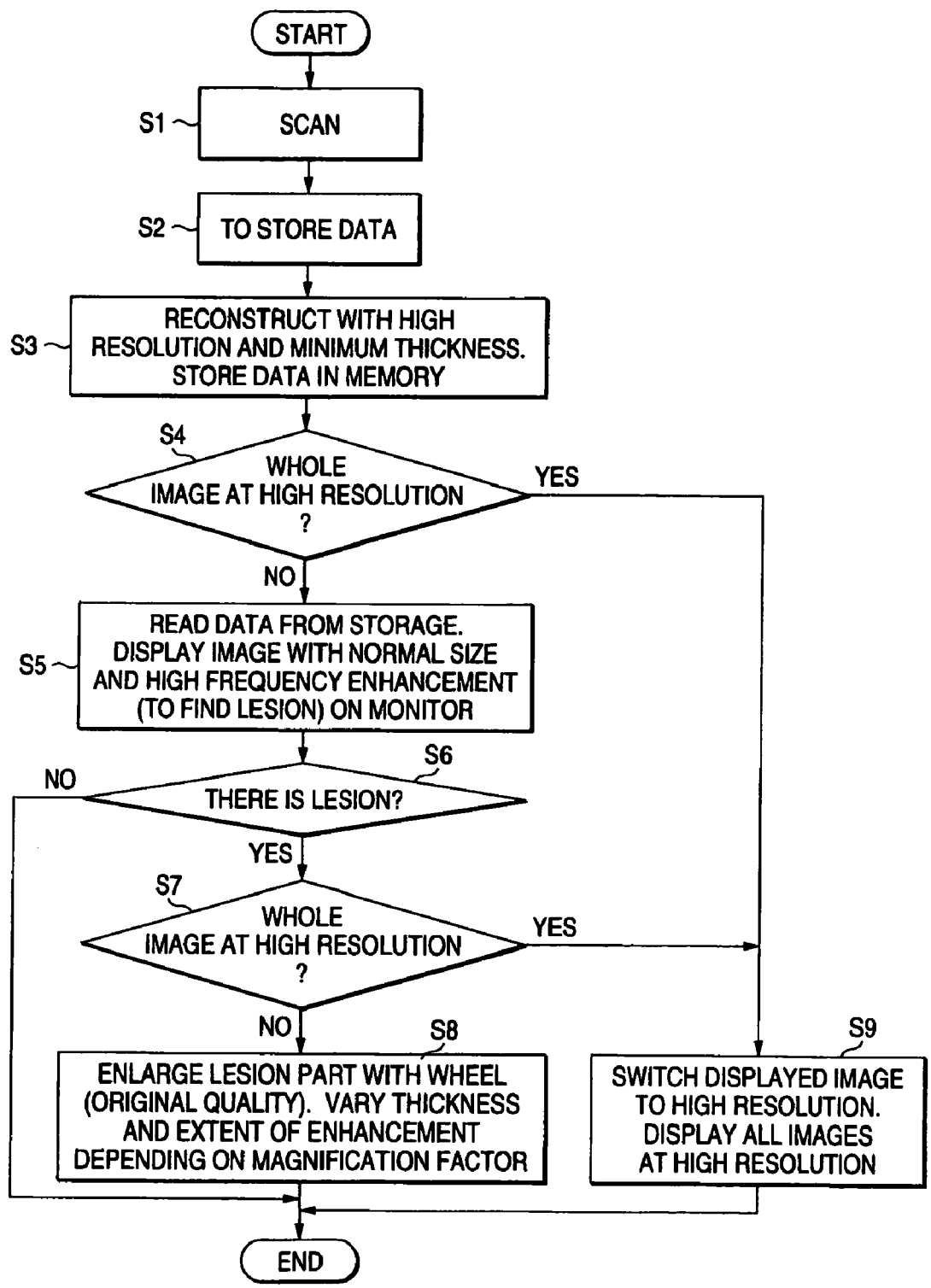
FIG. 3 is a flowchart illustrating a sequence of operations from scan to end of diagnostic reading according to the present embodiment of the invention.

FIG. 3 illustrates the flow (a sequence of operations) from scan performed by the X-ray CT scanner to end of diagnostic reading according to the present embodiment of the invention. Conditions (i.e., positioning, scan range, scan slice thickness, and helical pitch) are set in advance. After completion of the setting, helical or multislice scans are performed in practice to collect raw data from multiple directions within the scan range of the patient (step S1). The raw data is sent to the projection data storage circuit 20 from the X-ray detector 16 through the switches 17, data acquisition system 18, and data transfer circuit 19, and stored there (step S2). Based on the stored projection data, tomographic image data about plural slices centered at the specified slice position are reconstructed with the minimum image slice thickness (assumed to be 2 mm, in this embodiment) and maximum matrix size (assumed to consist of 1024×1024 pixels, in this embodiment) in the reconstruction calculation circuit 21. The data are stored in the image storage circuit 22 (step S3).

Then, a message for making an inquiry as to whether the whole image is displayed at high resolution or not is displayed on the monitor 29 together with "YES" and "NO" command buttons under control of the system control portion 5 (step S4). When the "YES" command button is clicked in step S4, a reconstruction is performed by the reconstruction calculation circuit 21 in step S3. All image data stored in the image storage circuit 22 are sent to the display storage circuit 27 under the conditions where the magnification factor is 1.0, i.e., the high resolution of 1024×1024 pixels is maintained. That is, neither magnification nor demagnification is performed by the image magnification-demagnification circuit 24. Also, slice images are not stacked. That is, the individual images are maintained with the number of slices set to 1 by the stack processing circuit 25. Furthermore, high-frequency components are not enhanced by the high-frequency enhancement circuit 26. The images are then displayed on the monitor 29 at high resolution via the display circuit 28 (step S9).

When the "NO" command button is clicked in step S4, the image data stored in the image storage circuit 22 are converted into a matrix size of 512×512 pixels by the image magnification-demagnification circuit 24 under the conditions where the magnification factor assumes a minimum value of 0.5. Data about five images around the slice position with the maximum number of slices of "5" are added by the stack processing circuit 25 (FIG. 4A). Furthermore, the data undergo the maximum extent, high-frequency enhancement by the high-frequency enhancement circuit 26 (FIG. 4B). The images are displayed at low resolution on the monitor 29 (step S5). Under conditions where the magnification factor assumes the minimum value of "0.5", an image of a wide range in the patient is displayed on the viewing screen (e.g., 512×512 pixels) of the monitor 29. This image has a large slice thickness of 10 mm, for example. In addition, the high-frequency components have been enhanced to a maximum extent. Therefore, it is easy to check whether there is any lesion. It is also easy to confirm the location.

Then, a message for making an inquiry as to whether there is a lesion is displayed on the monitor 29 together with the "YES" and "NO" command buttons under control of the system control portion 5 (step S6). When the "NO" command button is clicked, this diagnostic reading inspection ends. On the other hand, when the "YES" command button is clicked, a message for making an inquiry as to whether the whole image is displayed at high resolution is displayed on the monitor 29 along with the "YES" and "NO" command buttons (step S7). When the "YES" command button is clicked, the program goes to the step S9, and all images are displayed at high resolution on the monitor 29.

When the "NO" command button is clicked in step S7, the program proceeds to step S8. In the step S8, the diagnostic reader (human operator) moves the mouse 10 right, left, and back and forth on the mouse table to bring the pointer onto the lesion. The reader also rotates the wheel of the mouse 10 while holding the pointer at that position. A magnification factor corresponding to the number of rotations or rotational angle is entered. For example, whenever the wheel of the mouse 10 is rotated through 5°, the magnification factor increases in an increment of 0.05 within the range from the initial value of 0.5 to the maximum value of 1.0.

For example, when a magnification factor of 0.75 is entered, the matrix size of the tomographic image data stored in the image storage circuit 22 is converted into a matrix size of 768×768 pixels. Three slices around the slice position are stacked. The data undergo moderate high-frequency enhancement. The images are displayed about the position of the pointer on the monitor 29. Under the conditions where the magnification factor is a moderate value of 0.75, the lesion of the patient is displayed somewhat enlarged on the viewing screen of the monitor 29. This image has a general image slice thickness of 6 mm, for example. The high-frequency components are slightly enhanced. Accordingly, it is possible to identify the position of the lesion in further detail.

When a maximum magnification factor of 1.0 is entered by manipulating the wheel of the mouse 10, the tomographic image data stored in the image storage circuit 22 are displayed at high resolution around the position of the pointer on the monitor 29 while kept in high-resolution state (1024×1024 pixels) without undergoing either stacking processing or high-frequency enhancement (see FIG. 4C). Under conditions where the magnification factor assumes a maximum value of 1.0, the lesion of the patient is displayed enlarged on the viewing screen of the monitor 29. Furthermore, with respect to this image, the image slice thickness has a small value of 2 mm, for example. In addition, the high-frequency components are not enhanced or only slightly enhanced. Consequently, the tissue structure of the lesion can be checked in more detail.

As described so far, tomographic image data is reconstructed with a maximum matrix size and stored in memory. When the display magnification factor is modified, the matrix size is modified to cope with the tomographic image data previously reconstructed with the maximum matrix size. The image slice thickness is also modified similarly. The processing for modifying the matrix size and image slice thickness is much fewer in number of steps than the processing for reconstructing tomographic image data and hence the processing time can be shortened greatly. Accordingly, the wait time of the diagnostic reader can be shortened compared with the case where reconstruction of tomographic image data is repeated whenever the display magnification factor is modified as in the prior art. In consequence, the efficiency of the diagnostic reading work can be improved.

Furthermore, the image can be optimized for the purpose of the diagnostic reading that varies according to the magnification factor (such as identification of the position of a lesion or detailed diagnosis of the tissue structure) by automatically varying the extent of enhancement of the high-frequency components according to the magnification factor and automatically varying the number of stacked slices, i.e., the slice thickness. For this reason, the operation for setting the extent of enhancement of the high-frequency components is dispensed with, as well as the operation for setting the number of slices (slice thickness). The burden on the diagnostic reader during work can be alleviated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT scanner comprising:
   a gantry for collecting projection data about a patient;
   a reconstruction portion for reconstructing multislice image data or volumetric image data from said projection data at a given matrix size;
   a storage portion for storing said reconstructed image data;
   an input portion for entering a user's instruction regarding magnification or demagnification of image; and
   an image processing portion for converting the matrix size of said stored image data into a matrix size corresponding to said user's instruction and varying an image slice thickness of said storage image data into an image slice thickness corresponding to said user's instruction.

2. The X-ray CT scanner of claim 1, wherein the matrix size corresponding to said user's instruction is equal to or lower than the matrix size of said stored image data.

3. The X-ray CT scanner of claim 1, wherein the image slice thickness corresponding to said user's instruction is equal to or greater than the image slice thickness of said stored image data.

4. The X-ray CT scanner of claim 1, wherein said image processing portion enhances high-frequency components of said stored image data according to said user's instruction.

5. The X-ray CT scanner of claim 4, wherein said image processing portion enhances said high-frequency components relatively weakly when a user's instruction corresponding to a relatively high image magnification factor is entered and enhances said high-frequency components relatively strongly when a user's instruction corresponding to a relatively low image magnification factor is entered.

6. The X-ray CT scanner of claim 1, wherein said image processing portion sets said image slice thickness to a relatively small value when a user's instruction corresponding to a relatively high image magnification factor is entered and sets said image slice thickness to a relatively large value when a user's instruction corresponding to a relatively low image magnification factor is entered.

7. The X-ray CT scanner of claim 1, wherein said image processing portion sets the number of slices in said image data to a relatively small number when a user's instruction corresponding to a relatively high image magnification factor is entered and sets said number of slices to a relatively large number when a user's instruction corresponding to a relatively low image magnification factor is entered.

8. The X-ray CT scanner of claim 7, wherein said image processing portion sets the number of slices to 1 when a user's instruction corresponding to an image magnification factor of unity is entered.

9. The X-ray CT scanner of claim 1, wherein said image processing portion maintains the matrix size of said stored image data when a user's instruction corresponding to an image magnification factor of unity is entered.

10. The X-ray CT scanner of claim 1, wherein a numerical value indicative of an image magnification factor is entered or plural buttons corresponding to plural image magnification factors are selectively clicked as said user's instruction.

11. An image processor comprising:
a storage portion for storing multislice image data or volumetric image data about a patient;
an input portion for entering a user's instruction regarding magnification or demagnification of image; and
an image processing portion for converting a matrix size of said stored image data into a matrix size corresponding to said user's instruction and varying an image slice thickness of said stored image data into an image slice thickness corresponding to said user's instruction.

12. The image processor of claim 11, wherein the matrix size corresponding to said user's instruction is equal to or lower than the matrix size of said stored image data.

13. The image processor of claim 11, wherein the image slice thickness corresponding to said user's instruction is equal to or greater than the image slice thickness of said stored image data.

14. The image processor of claim 11, wherein said image processing portion enhances high-frequency components of said stored image data according to said user's instruction.

15. The image processor of claim 14, wherein said image processing portion enhances said high-frequency components relatively weakly when a user's instruction corresponding to a relatively high image magnification factor is entered and enhances said high-frequency components relatively strongly when a user's instruction corresponding to a relatively low image magnification factor is entered.

16. The image processor of claim 11, wherein said image processing portion sets said image slice thickness to a relatively small value when a user's instruction corresponding to a relatively high image magnification factor is entered and sets said image slice thickness to a relatively large value when a user's instruction corresponding to a relatively low image magnification factor is entered.

17. The image processor of claim 11, wherein said image processing portion sets the number of slices of said image data to a relatively small number when a user's instruction corresponding to a relatively high image magnification factor is entered and sets said number of slices to a relatively large number when a user's instruction corresponding to a relatively low image magnification factor is entered.

18. The image processor of claim 17, wherein said image processing portion sets said number of slices to 1 when a user's instruction corresponding to an image magnification factor of unity is entered.

19. The image processor of claim 11, wherein said image processing portion maintains the matrix size of said stored image data when a user's instruction corresponding to an image magnification factor of unity is entered.

20. The image processor of claim 11, wherein a numerical value indicative of an image magnification factor is entered or plural buttons corresponding to plural image magnification factors are selectively clicked as said user's instruction.

* * * * *